United States Patent [19]

Silver

[11] Patent Number: 5,565,442

[45] Date of Patent: Oct. 15, 1996

[54] STABILIZED PHARMACEUTICAL COMPOSITIONS CONTAINING DERIVATIVES OF VITAMINS D2 AND D3

[75] Inventor: David I. Silver, Givataim, Israel

[73] Assignee: Teva Pharmaceutical Industries Ltd., Jerusalem, Israel

[21] Appl. No.: 120,210

[22] Filed: Sep. 13, 1993

[30] Foreign Application Priority Data

Sep. 18, 1992 [IL] Israel ......................................... 103224

[51] Int. Cl.$^6$ .................................................. A61K 31/59
[52] U.S. Cl. ............................................ 514/167; 514/168
[58] Field of Search ....................................... 514/167, 168

[56] References Cited

U.S. PATENT DOCUMENTS

| | | |
|---|---|---|
| 3,932,634 | 1/1976 | Kardys . |
| 4,729,895 | 3/1988 | Makino et al. . |
| 4,929,610 | 5/1990 | Meier et al. ............................ 514/167 |

FOREIGN PATENT DOCUMENTS

| | | |
|---|---|---|
| 55165/90 | 11/1990 | Australia . |
| 69228/91 | 7/1991 | Australia . |
| 0177920 | 4/1986 | European Pat. Off. . |
| 0215596 | 3/1987 | European Pat. Off. . |
| 0387808 | 9/1990 | European Pat. Off. . |
| 0413828 | 2/1991 | European Pat. Off. . |
| 266099 | 3/1989 | German Dem. Rep. . |
| 3258722 | 11/1991 | Japan . |
| 3279324 | 12/1991 | Japan . |
| 4-74123 | 3/1992 | Japan . |
| 58206533 | 12/1993 | Japan . |
| WO91/16899 | 11/1991 | WIPO . |
| WO92/09271 | 6/1992 | WIPO . |

OTHER PUBLICATIONS

Fiedler, Dr. Herbert P. "Dictionary for Pharmaceutical, Cosmetical and Associated Fields", 3rd, Revised and Supplemented Edition. 1989.

*Primary Examiner*—Kimberly J. Prior
*Attorney, Agent, or Firm*—Cushman, Darby & Cushman

[57] ABSTRACT

The invention relates to a process for stabilizing pharmaceutically active derivatives of vitamin D2 and D3. At least one pharmaceutically active vitamin D derivative is dissolved in a solvent with an antioxidant. This solution is mixed with a pharmaceutically acceptable stabilizer and at least one solid pharmaceutical excipient or carrier which is present in an amount sufficient to impart the characteristics of a solid to the composition. Finally, the solvent is removed.

14 Claims, No Drawings

STABILIZED PHARMACEUTICAL COMPOSITIONS CONTAINING DERIVATIVES OF VITAMINS D2 AND D3

FIELD AND BACKGROUND OF THE INVENTION

The present invention relates to stabilized solid state pharmaceutical compositions containing an active component selected from pharmaceutically active derivatives of vitamin $D_2$ and vitamin $D_3$.

Derivatives of vitamin $D_2$ and vitamin $D_3$, which generally possess at least the activity of their underivatized precursors, have been found to be useful in medicine, e.g. they increase the serum calcium level, inhibit parathyroid hormone, and affect bone formation: they may also inhibit the proliferation of psoriatic and certain cancer cells. In particular, they are used to treat symptoms such as chronic renal failure, hypoparathyroidism, vitamin-D-resistant rickets, osteomalacia, osteoporosis and psoriasis.

However, such derivatives have the disadvantage of low stability under ordinary storage conditions. Moreover, refrigeration, protection against actinic radiation and replacement of the ambient atmosphere have not been found to be satisfactory as a means of stabilization and are often costly. Consequently, various stabilization methods have been proposed. Thus, by way of example, EP 413828A teaches dispersion of active ingredient in an excipient readily soluble in organic solvent and a basic substance, EP 387808A uses a stabilizer selected from polyvinylacetal diethylaminoacetate and hydroxypropylcellulose, while JP 258722/91 discloses compositions containing crystalline cellulose and butylated hydroxytoluene (BHT) or butylated hydroxyanisole (BHA), as antioxidant. JP 074123/92 discloses compositions containing active forms of vitamin $D_3$ and gelatin in the same phase; in an example of a liquid phase composition, a polyoxyethylene hardened castor oil derivative was also present.

All of these exemplary solid pharmaceutical compositions show unsatisfactory stability at elevated temperatures or/and humidities. Consequently, there is a great need for improved stabilized solid state pharmaceutical compositions containing the ingredients referred to above.

Accordingly, it is an object of the invention to provide solid pharmaceutical compositions containing an active component selected from pharmaceutically active derivatives of vitamin $D_2$ and vitamin $D_3$, which exhibit improved stability for a prolonged period of time. Other objects of the invention will appear from the description which follows.

SUMMARY OF THE INVENTION

The present invention accordingly provides in one aspect, a solid state pharmaceutical composition which comprises at least ingredients (a), (b) and (c) of the following ingredients (a), (b), (c) and (d), namely: (a) at least one active component selected from pharmaceutically active derivatives of vitamin $D_2$ and vitamin $D_3$; (b) at least one pharmaceutically acceptable antioxidant; (c) at least one pharmaceutically acceptable polyoxyalkyl stabilizer; (d) at least one solid pharmaceutical excipient or carrier in an amount sufficient to impart the characteristics of a solid to the composition.

In another aspect, the present invention provides a process for preparing the pharmaceutical composition as defined in the preceding paragraph, which comprises the sequential steps of: (i) dissolving ingredients (a) and (b) in a solvent; (ii) thoroughly mixing the solution formed in step (i) with ingredients (c), and with ingredient (d) when this is present; and (iii) removing the solvent.

DETAILED DESCRIPTION OF THE INVENTION

The product of the process just described may be granulated; if desired, the granulate may then be formed into a dosage form selected from tablets, sachets and gelatin capsules (e.g. hard gelatin capsules). A lubricant such as magnesium stearate and/or calcium stearate may be added at any convenient stage. It will be appreciated that in the alternative, the product of the process described above need not be granulated, but may be obtained as a uniform dry powder, which is then mixed with lubricant if desired, and then made into dosage forms such as those specified above. In order to avoid premature deterioration of the composition, it is preferred to remove the solvent under mild conditions, e.g. at ambient temperature, and in the presence of an inept atmosphere (such as nitrogen) or in vacuum.

Presently preferred ingredients of the solid state pharmaceutical composition of the invention are:

(a) 1α-hydroxycholecalciferol (1α-(OH)$D_3$), 24-hydroxycholecalciferol (24-(OH)$D_3$), 25-hydroxycholecalciferol (25-(OH)$D_3$), 1α,25-dihydroxycholecalciferol (1α,25-(OH)$_2D_3$), 1α,24-dihydroxycholecalciferol (1α,24-(OH)$_2D_3$), 24,25-dihydroxycholecalciferol (24,25-(OH)$_2D_3$), 1,24,25-trihydroxycholecalciferol (1,24,25-(OH)$_3D_3$), 1α-hydroxyergocalciferol (1α-(OH)$D_2$) and 1α,25-dihydroxyergocalciferol (1α,25-(OH)$_2D_2$);

(b) butylated hydroxytoluene (BHT), butylated hydroxyanisole (BHA), vitamin E, propyl gallate, β-carotene and ascorbic acid;

(c) polyethyleneglycois, polyethyleneglycol ethers, polyethyleneglycol esters, polyoxyethylated castor oil, polyoxyethylated hydrogenated castor oil (e.g. Cremophor RH, a Trade Mark of BASF AG), polyoxyethylated sorbitan fatty acid esters and polyoxyethylated glycerol fatty acid esters;

(d) lactose, sorbitol and calcium phosphate.

As regards the proportions of the ingredients which may be used in the solid state pharmaceutical compositions of the invention, it will be evident that since use of a pharmaceutical excipient or carrier, i.e. optional ingredient (d), is conventional, the proportions in which it may be used, if desired, in the present invention are also conventional. The essential ingredients (a), (b) and (c) may be used in proportions which may be varied within wide ranges.

Active ingredient (a), when used in a composition of the invention intended for direct therapeutic application (in the usual dosage forms), may be present in an amount within the range of e.g. 0.0000025 to 5.0 wt. %, but more usually 0.0005 to 1.0 wt. %. However, it is also within the contemplation of the present invention that the compositions may be in the form of concentrates of active ingredient, prior to preparation of finished dosage forms, in which case up to 25, or even up to 50 wt % of ingredient (a), may be present.

Antioxidant ingredient (b) may be present in an amount within the range of e.g. 0.0000025 to 10.0 wt. %, but more usually 0.0025 to 1.0 wt. %. As is of course well known in the pharmaceutical art, the amount of antioxidant used will also take account of the relative toxicity of a particular antioxidant.

Polyoxyalkyl stabilizer, ingredient (c), may be present in an amount within the range of e.g. 0.01 to 50 wt. % in a composition intended for therapeutic administration. In this connection, reference may be made the Examples set forth below in which the amount of ingredient (c) varies between 3 and more than 21 wt. % of the total composition. However, as may also be seen from the Examples, the proportion of ingredient (c) may approach 100%, when ingredient (d) is omitted.

It is presently preferred that, when ingredient (d) is present, the compositions comprise (by weight) 0.00003 to 0.8% (a), 0.01 to 0.1% (b) and 0.03 to 30% (c); and corresponding relative proportions of (a), (b) and (c), when ingredient (d) is absent. In other words, according to a presently preferred embodiment, the relative weight patio ranges of ingredients (a), (b) and (c) are 0.00003 to 0.8 (a): 0.01 to 0.1 (b): 0.03 to 30 (c), respectively, whether or not ingredient (d) is present.

The invention will now be illustrated by the following non-limitative Examples. It may be noted in passing that the invention includes additionally the compositions specified in Examples 1–5, but from which the excipients (lactose or sorbitol) and lubricant (magnesium stearate) have been excluded.

EXAMPLE 1

Butylated hydroxyanisole (557 mg) and 1α-OH-$D_3$ (5.1 mg) were dissolved in ethanol (300 g). The solution was mixed for 20 minutes with sorbitol (1.8 kg) and polyoxyethylated hydrogenated castor oil (55.69 g) in a high speed mixer, the residual ethanol solution being washed into the mixer with an additional 50 g ethanol. The resulting wet mass was removed and dried on trays under vacuum with a nitrogen bleed at ambient temperature, to give dry granules which were screened (30 mesh) and mixed with magnesium stearate (4.64 g). These granules can be packed into sachets or hard gelatin capsules, or pressed into tablets, by conventional methods. The product contained the ingredients in the following percentages by weight:

| | |
|---|---|
| polyoxyethylated hydrogenated castor oil | 2.99% |
| 1α-OH-$D_3$ | 0.00027% |
| butylated hydroxyanisole | 0.0299% |
| sorbitol | 96.73% |
| magnesium stearate | 0.25% |

Examples 2–5 were carried out similarly (except where indicated), but contained the ingredients as described below, in which the stated percentages are by weight.

EXAMPLE 2

In this Example, the lactose and magnesium stearate are omitted prior to the drying step. The lactose- and magnesium stearate-free product is then thoroughly mixed with these two ingredients prior to tabletting.

| | |
|---|---|
| polyethylene glycol 6000 | 21.25% |
| 24,25(OH)$_2$$D_3$ | 0.011% |
| butylated hydroxyanisole | 0.04% |
| lactose | 78.47% |
| magnesium stearate | 0.25% |

EXAMPLE 3

| | |
|---|---|
| polyoxyethylated hydrogenated castor oil | 3.0% |
| 24,25(OH)$_2$$D_3$ | 0.088% |
| butylated hydroxyanisole | 0.03% |
| sorbitol | 96.63% |
| magnesium stearate | 0.25% |

EXAMPLE 4

| | |
|---|---|
| polyoxyethylated hydrogenated castor oil | 3.0% |
| 24,25(OH)$_2$$D_3$ | 0.01% |
| butylated hydroxyanisole | 0.03% |
| sorbitol | 96.71% |
| magnesium stearate | 0.25% |

EXAMPLE 5

| | |
|---|---|
| polyoxyethylated hydrogenated castor oil (Cremophor RH40) | 4.0% |
| 1α-OH-$D_3$ | 0.000373% |
| butylated hydroxyanisole | 0.04% |
| sorbitol | 95.96% |

Stability Tests

The exemplified solid state pharmaceutical compositions in tablet form were stored at 40° C. and 75% relative humidity. Assay of the active ingredient at monthly intervals gave the following results, expressed as a percentage of the initial assay.

| Months | Example 1 | Example 2 | Example 3 | Example 4 |
|---|---|---|---|---|
| 0 | 100.0 | 100.0 | 100.0 | 100.0 |
| 1 | 105.0 | — | 99.1 | 100.0 |
| 2 | 101.7 | — | 95.9 | 102.0 |
| 3 | 98.98 | 91.3 | 96.0 | 98.8 |
| 4 | 102.0 | — | 98.2 | 97.4 |
| 5 | 98.15 | — | — | — |
| 6 | 99.2 | — | 91.2 | 95.1 |

The excellent results of stability tests shown above by solid state pharmaceutical compositions in accordance with the present invention may be contrasted with the above-mentioned prior art, which may be summarized as follows, from which it may also be noted that no results were given for any period of time longer than one month.

EP 413828A: at 40° C. and 75% relative humidity (as in the present stability tests), assay was 95–100% at 7 days, 93–99% at 14 days and 91–94% at 30 days.

EP 387808A: 50 ° C., assay was 98.0–98.8% at two weeks and 95.7–97.5% at four weeks.

JP 258722/91: after one month at 40° C., assayed 97.82 or 97.18% vitamin $D_3$, which is not directly comparable with the present active compounds (data on exemplified 1α-OH-$D_3$ not supplied).

JP 074123/92: after 7 and 14 days at 60° C., a liquid phase composition assayed 95.4 or 81.7% 1α-OH-$D_3$.

It will be appreciated by persons skilled in the art that the present invention is not restricted to the embodiments which have been particularly described hereinabove, but that many modifications and variations may be made. Thus, the invention may be practised in accordance with its scope, concept and spirit, as will be appreciated by skilled persons, after reading the present specification and the appended claims.

I claim:

1. A process for stabilizing at least one active component selected from pharmaceutically active derivatives of vitamins $D_2$ and vitamin $D_3$, which comprises the step of compositing said component with at least one pharmaceutically acceptable antioxidant, at least one pharmaceutically acceptable polyoxyalkyl stabilizer and at least one solid pharmaceutical excipient or carrier in an amount sufficient to impart the characteristics of a solid to the composition thus produced;

wherein said step of compositing includes the sequential steps of dissolving said at least one active component and said at least one pharmaceutically acceptable antioxidant in a solvent, thoroughly mixing the resulting solution with said at least one pharmaceutically acceptable stabilizer and said at least one solid pharmaceutical excipient or carrier and removing the solvent;

provided that said antioxidant and said polyoxyalkyl stabilizer are present in the resultant composition in amounts which together are effective to stabilize said active component.

2. A process according to claim 1, wherein at least one of the following conditions (i), (ii) and (iii) is fulfilled:

(i) said active component is selected from 1α-hydroxycholecalciferol, 24-hydroxycholecalciferol, 25-hydroxycholecalciferol, 1α,25-dihydroxycholecalciferol, 1α,24-dihydroxycholecalciferol, 24,25-dihydroxycholecalciferol, 1,24,25-trihydroxycholecalciferol, 1α-hydroxyergocalciferol and 1α,25-dihydroxyergocalciferol;

(ii) said antioxidant is selected from butylated hydroxytoluene (BHT), butylated hydroxyanisole (BHA), vitamin E, propyl gallate, β-carotene and ascorbic acid;

(iii) said polyoxyalkyl stabilizer is selected from polyethyleneglycols, polyethyleneglycol ethers, polyethyleneglycol esters, polyoxyethylated castor oil, polyoxyethylated hydrogenated castor oil, polyoxyethylated sorbitan fatty acid esters and polyoxyethylated glycerol fatty acid esters.

3. A process according to claim 2, wherein at least one of the following conditions (α) and (β) is fulfilled:

(α) the relative weight ratio ranges of said active component, said antioxidant and said polyoxyalkyl stabilizer are 0.00003 to 0.8 active component: 0.01 to 0.1 antioxidant: 0.03 to 30 polyoxyalkyl stabilizer, respectively;

(β) said composition is formulated in a form selected from powders, granules, tablets, sachets and gelatin capsules.

4. A process according to claim 3, wherein said removing of solvent is carried out at ambient temperature, in an inert atmosphere or in vacuum.

5. A process according to claim 1, wherein at least one of the following conditions (i), (ii) and (iii) is fulfilled:

(i) said active component is selected from 1α-hydroxycholecalciferol and 24,25-dihydroxycholecalciferol;

(ii) said antioxidant is selected from butylated hydroxytoluene (BHT), butylated hydroxyanisole (BHA), vitamin E, propyl gallate, β-carotene and ascorbic acid;

(iii) said polyoxyalkyl stabilizer is selected from polyethyleneglycols, polyethyleneglycol ethers, polyethyleneglycol esters, polyoxyethylated castor oil, polyoxyethylated hydrogenated castor oil, polyoxyethylated sorbitan fatty acid esters and polyoxyethylated glycerol fatty acid esters.

6. A process according to claim 5, wherein at least one of the following conditions (α) and (β) is fulfilled:

(α) the relative weight ratio ranges of said active component, said antioxidant and said polyoxyalkyl stabilizer are 0.00003 to 0.8 active component: 0.01 to 0.1 antioxidant: 0.03 to 30 polyoxyalkyl stabilizer, respectively;

(β) said composition is formulated in a form selected from powders, granules, tablets, sachets and gelatin capsules.

7. A process according to claim 6, wherein said removing of solvent is carried out at ambient temperature, in an inept atmosphere or in vacuum.

8. A process according to claim 1, wherein at least one of the following conditions (α) and (β) is fulfilled:

(α) the relative weight ratio ranges of said active component, said antioxidant and said polyoxyalkyl stabilizer are 0.00003 to 0.8 active component: 0.01 to 0.1 antioxidant: 0.03 to 30 polyoxyalkyl stabilizer, respectively;

(β) said composition is formulated in a form selected from powders, granules, tablets, sachets and gelatin capsules.

9. A process according to claim 8, wherein said removing of solvent is carried out at ambient temperature, in an inert atmosphere or in vacuum.

10. A process according to claim 1, wherein said at least one solid pharmaceutical excipient or carrier is selected from the group consisting of lactose, sorbitol and calcium phosphate.

11. A product made by the process of claim 10 consisting of (1) at least one active component selected from pharmaceutically active derivatives of vitamin $D_2$ and vitamin $D_3$; (2) at least one pharmaceutically acceptable antioxidant; (3) at least one pharmaceutically acceptable polyoxyalkyl stabilizer; and (4) at least one solid pharmaceutical excipient or carrier in an amount sufficient to impart the characteristics of a solid to the composition.

12. A process according to any one of claims 1 to 7, wherein said composition also comprises at least one member selected from the group consisting of magnesium stearate, calcium stearate and other pharmaceutical lubricants.

13. A product made the process of claim 12 consisting of (1) at least one active component selected from pharmaceutically active derivatives of vitamin $D_2$ and vitamin $D_3$; (2) at least one pharmaceutically acceptable antioxidant; (3) at least one pharmaceutically acceptable polyoxyalkyl stabilizer; and (4) at least one solid pharmaceutical excipient or carrier in an amount sufficient to impart the characteristics of a solid to the composition.

14. A product made by the process of any one of claims 1 to 7 consisting of (1) at least one active component selected from pharmaceutically active derivatives of vitamin $D_2$ and vitamin $D_3$; (2) at least one pharmaceutically acceptable antioxidant; (3) at least one pharmaceutically acceptable polyoxyalkyl stabilizer; and (4) at least one solid pharmaceutical excipient or carrier in an amount sufficient to impart the characteristics of a solid to the composition.

\* \* \* \* \*